United States Patent [19]

Buysch et al.

[11] Patent Number: 4,816,576

[45] Date of Patent: Mar. 28, 1989

[54] SULPHONIC ACID AMIDAMINES

[75] Inventors: Hans-Josef Buysch, Krefeld; Wolfgang Wellner, Cologne; Hermann Gruber, Leverkusen, all of Fed. Rep. of Germany

[73] Assignee: Bayer Akteingesellschaft, Leverkusen, Fed. Rep. of Germany

[21] Appl. No.: 877,244

[22] Filed: Jun. 23, 1986

Related U.S. Application Data

[63] Continuation of Ser. No. 489,047, Apr. 27, 1983, abandoned.

[30] Foreign Application Priority Data

May 8, 1982 [DE] Fed. Rep. of Germany ....... 3217372

[51] Int. Cl.⁴ .................. C07D 241/04; C07C 143/72
[52] U.S. Cl. ..................................... 544/398; 544/401; 544/402; 564/82; 564/83; 564/95; 564/96; 564/98
[58] Field of Search .................. 564/82, 83, 95, 96, 564/98; 544/398, 401, 402

[56] References Cited

U.S. PATENT DOCUMENTS

| | | | |
|---|---|---|---|
| 2,321,890 | 6/1943 | Berchet | 564/95 X |
| 3,346,553 | 10/1967 | Kuhne et al. | 564/95 X |
| 3,753,996 | 8/1973 | Naito | 564/95 X |
| 4,056,523 | 11/1977 | Mischke | 564/95 X |
| 4,122,266 | 10/1978 | de Vries | 564/80 UX |

Primary Examiner—Paul F. Shaver

Attorney, Agent, or Firm—Connolly and Hutz

[57] ABSTRACT

The invention relates to a sulphonic acid amidamine corresponding to the following general formula I:

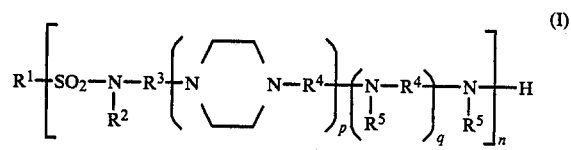

wherein
- $R^1$ represents a $C_8$–$C_{30}$ linear, saturated aliphatic hydrocarbon group or said group which is substituted by one or more chlorine atoms;
- $R^2$ and $R^5$ independently represent hydrogen or $C_1$–$C_6$ alkyl or $C_1$–$C_6$ alkyl which is substituted with one of the groups: hydroxyl, amino, mercapto, cyano, carboxyl or carbamoyl, and/or is interrupted by at least one oxy (—O—) or thio (—S—) group;
- $R^3$ and $R^4$ independently represent $C_2$–$C_{13}$ alkylene or $C_5$–$C_7$ cycloalkylene or said alkylene or cycloalkylene groups which are substituted with one of the groups: hydroxyl, amino, mercapto, cyano, carboxyl or carbamoyl;
- p represents zero or an integer of from 1 to 3;
- q represents zero or an integer of from 1 to 12; and
- n represents an integer of from 1 to 8.

4 Claims, No Drawings

SULPHONIC ACID AMIDAMINES

This is a continuation of application Ser. No. 489,047 filed Apr. 27, 1983, now abandoned.

This invention relates to aliphatic, saturated sulphonic acid amidamines, to the production thereof from the corresponding sulphonic acid aryl esters by a reaction with diamines and higher polyamines, which have at least two aliphatic amino groups each containing at least one active hydrogen atom, and to the use of the sulphonamidamines as modifiers and hardeners for compounds containing at least one 1,2-epoxide group.

According to German Auslegeschrift No. 1,076,366, aliphatic polysulphonic acid amides or aromatic sulphonic acid amides still containing primary aromatic amino groups may be used as hardeners for epoxide resins. These substances, however, are generally solid products and must be dissolved hot in the epoxide resin. Even when miscibility good, complete hardening of the epoxide resin mass is only achieved after several hours heating to from 140° to 160° C.

According to U.S. Pat. No. 2,510,886, column 5, lines 30–34, sulphonic acid amides, such as p-toluene sulphonic acid amide or naphthalene sulphonic acid amides, may be converted into insoluble, infusible moulded articles by treating them with mixtures of Polyfunctional phenols and polyepoxide compounds (see also U.S. Pat. No. 2,712,001).

It is also known from U.S. Pat. No. 3,501,533 that polyepoxides containing more than one 1,2-epoxide group may be hardened by copolymers of vinyl or vinylidene monomers and vinyl sulphonic acid amides at from 120° to 230° C., preferably in the presence of a catalyst. The aforesaid copolymers are solid and must be mixed with the polyepoxides in the molten state or dissolved in organic solvents. Cold setting is virtually impossible.

Furthermore, in U.S. Pat. No. 4,122,266 it has been disclosed to prepare inter alia $C_{35}$-$C_{350}$ alkane sulphonic acid amidamines and to use them as lubricant oil additives.

The requirements of hardeners for epoxide resins, in particular in the field of lacquers, are progressively in the direction of avoiding not only toxic and expensive solvents, but all organic solvents and of finding low viscosity formulations, but these are only possible if the hardeners are themselves fairly fluid. In addition, increasing importance is attached to systems which may be both formulated with epoxide resins as such and also made up into systems which may be diluted with water. Moreover, it is desired to have such systems available not only as heat setting, but also as cold setting, systems. For large surface areas, e.g. in the building sector, cold setting is indeed an essential pre-condition for the successful use of epoxide resin systems. Various types of aliphatic amines are available for this purpose. Although these are suitable for cold setting, the lacquer films obtained generally form unsightly, tacky, irregular and not completely hardened surface masses (blooming effect). Furthermore, such epoxide resin masses are generally relatively brittle.

Epoxide resin lacquers which are exceptionally elastic, but therefore also soft, are obtained by using polyamidamines of dimeric fatty acids and polyalkylene polyamines, although these hardeners are solid substances which may only be used in combination with solvents. Water-dilutable systems on this basis have therefore recently been developed with a view to avoiding the use of organic solvents. The consequence of this, however, is that such systems may only be applied in relatively thin layers and cannot be filled with the conventional solid additives and pigments because the water used for diluting the mass would then not be able to escape.

It was therefore an object of the present invention to find hardeners and modifiers for epoxide compounds containing at least one 1,2-epoxide group, which agents would have a relatively low viscosity so that they could be used for solvent-free lacquer and coating formulations, optionally containing pigments and/or fillers, but at the same time the compositions of hardener and polyepoxide should be capable of being diluted with water, regardless of the consistency thereof. Furthermore, the compositions should harden rapidly even at room temperature and result in coatings and lacquers having a smooth, glossy, tack-free surface and a good balance between hardness and elasticity.

The problem was solved by using certain aliphatic, saturated sulphonic acid amidamines, as defined below, as modifying agents and hardeners.

The present invention thus relates to sulphonic acid amidamines corresponding to the following general formula (I):

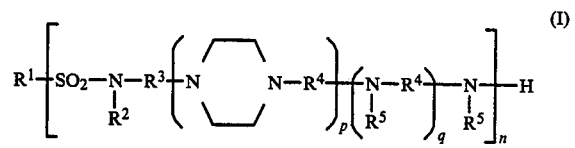

wherein
$R^1$ represents a linear, saturated, aliphatic hydrocarbon group having from 8 to 30 carbon atoms or said group which is substituted by one or more chlorine atoms;

$R^2$ and $R^5$, which may be the same or different, represent hydrogen or an alkyl group having from 1 to 6 carbon atoms, or said alkyl group which is substituted with one of the groups: hydroxyl, amino, mercapto, cyano, carboxyl or carbamoyl, or interrupted by at least one oxy(—O—) or thio (—S—) group;

$R^3$ and $R^4$, which may be the same or different, represent an alkylene group having from 2–13 carbon atoms or a cycloalkylene group having from 5 to 7 carbon atoms or said alkylene or cycloalkylene group which are substituted with the same groups as $R^2$ and $R^5$;

p represents zero or an integer of from 1 to 3;
q represents zero or an integer of from 1 to 12; and
n represents an integer of from 1 to 8; or mixtures thereof.

$R^1$ preferably represents a linear, saturated, aliphatic hydrocarbon group having from 10 to 18 carbon atoms; $R^2$ and $R^5$ preferably represent hydrogen; $R^3$ and $R^4$ preferably represent an alkylene group having 2 or 3, preferably 2, carbon atoms; p preferably represents 0, 1 or 2, in particular 0; q represents an integer of from 1 to 6; and n represents an integer of from 1 to 5.

One important, unforeseeable advantage of the present alkane sulphonic acid amidamines compared with comparable alkane carboxylic acid amidamines resides in the fact that, while containing a comparable number of NH equivalents, the alkane sulphonic acid amidamines are liquid, have a surprisingly low viscosity, are readily soluble in the conventional lacquer solvents, such as xylene, butyl acetate, isopropanol, butanol and ethyl glycol acetate, and have excellent compatibility with the common commercial epoxide resins. In spite of the remarkable miscibility thereof with many organic compounds ranging from the polar to the apolar, the alkane sulphonic acid amidamines generally have excellent solubility in water.

Such aqueous solutions of alkane sulphonic acid amidamines according to the present invention are surprisingly capable of emulsifying epoxide resins without the aid of high speed stirrers or additional emulsifiers, simply by stirring them using conventional stirrers, so that they provide an elegant solution to formulating highly fluid, environmentally harmless cold setting epoxide resin systems which may be diluted with water.

Compared with these alkane sulphonic acid amidamines, alkane carboxylic acid amidamines having a comparable structure and number of NH equivalents have a waxy to hard and solid consistency, are insoluble in most organic solvents, at least in the cold, and are also insoluble in cold water and incompatible with the common commercial epoxide resins. These alkane carboxylic acid amidamines have nevertheless been used to prepared hardened epoxide resin films, albeit under conditions quite different from those which would be found in practice. The thus-obtained films are cloudy, unsightly, tacky and not completely hardened.

Alkane sulphonic acid amidamines have one further unforseeable characteristic. The reactivity thereof progresses in a series which runs counter to the functionality thereof, that is to say, the lower the number of reactive NH groups in a molecule of the hardener, the higher is the reactivity of the epoxide-hardener mixtures. The very opposite was to be expected.

The sulphonic acid amidamines corresponding to general formula (I) are generally mixtures of various sulphonic acid amidamines. This is partly due to the fact, that for economic reasons, the polyamine is not reacted with pure alkane sulphonic acid esters to produce the sulphonic acid amidamines, but with commercial mixtures which may contain the corresponding di-, tri-, tetra- and penta-sulphonic acid esters in addition to the particular alkane monosulphonic acid ester. In addition, the polyamine is frequently not one specific polyamine, but a mixture of several polyamines. One particularly preferred polyamine is pentaethylene hexamine and mixtures thereof with triethylene tetramine and/or tetraethylene pentamine and higher polyamines, such as octaethylene nonamines. Due to the production thereof (from dichloroethane and ammonia), the polyamines may also contain piperazine structures in the molecular chain.

The compounds corresponding to general formula (I) may be produced by reacting sulphonic acid derivatives corresponding to the following general formula (II):

$$R^1(SO_2X)_n \quad (II)$$

wherein
$R^1$ and $n$ are as defined in connection with general formula (I); and
X represents -O-aryl, preferably O-phenyl or O-cresyl;
with amines corresponding to the following general formula (III):

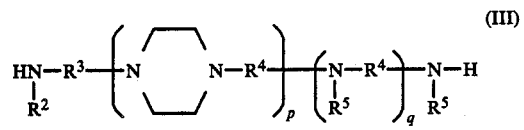

wherein $R^2$, $R^3$, $R^4$, $R^5$, p and q are as defined in connection with general formula (I); at temperatures of from 80 to 280° C., preferably from 100° to 250° C., optionally in the presence of catalysts. The HX group split off in the process may be partly or completely left in the reaction mixture or it may be removed. The amine (III) is preferably used in a quantity of from 0.3 to 3.0 mol per equivalent of sulphonate ester. Any excess of polyamine put into the process may be left in the reaction product or removed by distillation.

For hardening polyepoxides, the sulphonamidamines according to the present invention may advantageously also be used as mixtures with the polyamines used as starting components. In that case, the mixtures may consist of from 30 to 70 mol % of sulphonamidamine (I) and from 70 to 30 mol % of the polyamines (III) used for producing the sulphonamidamines.

The products according to the present invention may also be used as mixtures with other epoxide hardeners, such as isophorone diamine or diamino-dicyclohexylmethane.

The sulphonic acid amidamines according to the present invention may also be produced from the corresponding $C_8$-$C_{30}$ alkane sulphochlorides and the amines corresponding to general formula (III).

The sulphonic acid esters used as starting materials are known and may be obtained, for example, by the process according to U.S. Pat. No. 2,683,161.

If desired, the sulphonic acid amidamines according to the present invention corresponding to general formula (I) (1 mol) may also be reacted with from 0.5 to 2.3 mol, preferably from 0.8 to 1.9 mol, of a saturated lactam, in particular ε-caprolactam, and/or from 0.5 to 2.8 mol, preferably from 0.6 to 2.5 mol, of acrylonitrile, methacrylonitrile or mixtures thereof. The sulphonic acid amidamines according to the present invention (1 mol) may also be modified with from 0.01 to 1.8 mol, preferably from 0.1 to 1.6 mol, of a 1,2-alkylene oxide, such as ethylene oxide, propylene oxide or phenyl glycidyl ether. The reactions mentioned above may also be carried out by the process indicated in U.S. Pat. No. 4,263,162.

The hardeners according to the present invention vary from thin liquids to viscous oils or resins which may be mixed with up to 20%, by weight, of a suitable diluent or with water further to reduce the viscosity. The hardeners have amine equivalents (=NH equivalents) of from 40 to 300, the amine equivalent being the quotient of the molecular weight of the product and the number of hydrogen atoms attached to the amine nitrogen, not counting hydrogen atoms which are attached to sulphonyl amino (—SO_2—NH—) groups.

The hardeners according to the present invention may be used not only like the conventional aliphatic polyamines or polyamidamines for hardening polyepoxides in the heat or in thick layers at room temperature, but may also be used for hardening polyepoxides in thin layers (thickness below 0.5 cm) at room temperature, and tack-free, dust-dry, clear glossy films and coatings having a flawless surface are frequently obtained after only from 6 to 12 hours.

The hardeners according to the present invention may be used for hardening in quantities of from 0.6 to 1.5, preferably from 0.8 to 1.2, amine equivalents (=NH equivalents) per epoxide equivalent.

By "epoxide equivalent" is meant the quantity of 1,2-epoxide compound containing one 1,2-epoxide group. The epoxide value therefore represents the number of 1,2-epoxide groups contained in 100 g of epoxide groups.

The epoxides may be the conventional polyepoxides containing more than one 1,2-epoxide group. These include, polyglycidyl ethers of polyfuntional phenols, for example, polyglycidyl ethers of pyrocatechol, resorcinol, hydroquinone, of 4,4'-dihydroxy-diphenyl-methane, of 4,4'-dihydroxy-3,3'-dimethyl-diphenyl-methane, of 4,4'-dihydroxy-diphenyl-dimethylmethane (bisphenol A), of 4,4'-dihydroxy-diphenyl-methyl-methane, of 4,4'-dihydroxy-diphenyl-cyclohexane, of 4,4'-dihydroxy-3,3'-dimethyl-diphenyl-propane, of 4,4'-dihydroxy-diphenyl, of 4,4'-dihydroxy-diphenylsulphone, of tris-(4-hydroxy-phenyl)-methane, of the chlorination and bromination products of the abovementioned diphenols, in particular of bisphenol A; polyglycidyl ethers of Novolacs (i.e. of reaction products of mono- or polyfunctional phenols with aldehydes, in particular formaldehyde, in the presence of acid catalysts), of diphenols which have been obtained by the esterification of 2 mols of the sodium salt of an aromatic hydroxy-carboxylic acid with 1 mol of a dihalo-alkane or dihalo-dialkyl ether (see British Patent No. 1,017,612), and of polyphenols which have been obtained by the condensation of phenols with longcahin halogenated paraffins containing at least two halogen atoms (see British Pat. No. 1,024,288).

Apart from epoxide resins based on a polyfunctional phenol and a chlorinated epoxide compound, epoxidized ring compounds according to U.S. Pat. No. 2,716,123 may be used.

Glycidyl ethers of polyhydric alcohols, for example, of 1,4-butane diol, 1,4-butene diol, glycerol, trimethylol propane, pentaerythritol and polyethylene glycols are also suitable.

Triglycidyl isocyanurate, N,N'-diepoxy-propyloxamide, polyglycidyl thioethers of polyfunctional thiols, such as bis-ercaptomethyl-benzene, diglycidyl-trimethylene-trisulphone, epoxidized polybutadiene, epoxidized linseed oil and vinyl cyclohexene-diepoxide are also of interest.

The following may also be used: glycidyl esters of polybasic aromatic, aliphatic and cycloaliphatic carboxylic acids, for example, phthalic acid diglycidyl ester, terephthalic acid diglycidyl ester, tetrahydrophthalic acid diglycidyl ester, adipic acid diglycidyl ester, hexahydrophthalic acid diglycidyl ester optionally substituted by methyl groups, and glycidyl esters of reaction products of 1 mol of an aromatic or cycloaliphatic dicarboxylic acid anhydride and ½ mol of a diol or 1/n mol of a polyol containing n hydroxyl groups, such as glycidyl carboxylic acid esters corresponding to the following general formula:

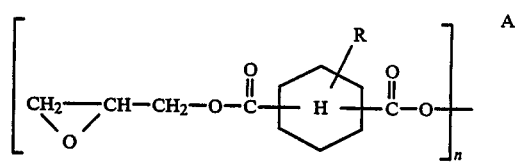

wherein A represents an at least divalent residue of an aliphatic hydrocarbon optionally interrupted one or more times by oxygen atoms and/or by cycloaliphatic rings, or the divalent residue of a cycloaliphatic hydrocarbon; R represents hydrogen or an alkylene group having from 1 to 3 carbon atoms; and n represents an integer of from 2 to 6; or mixtures of the glycidyl carboxylic acid esters corresponding to the above general formula (see British Patent No. 1,220,702).

Also of interest are epoxide resins which have been reacted with monocarboxylic acids, in particular with fatty acids, such as the epoxide resins of linseed oil, soya bean oil, saffron oil, perilla oil, tung oil, poppy seed oil, sunflower oil, tall oil, walnut oil, dehydrated castor oil, herring oil. The epoxide resins may easily be esterified by heating under reflux in the presence of one or more carboxylic acids, while removing water azeotropically.

Polyglycidyl ethers of Polyfunctional phenols and polyhydric alcohols, as well as glycidyl esters, in particular polyepoxides based on bisphenol A, are preferred.

The resin compositions of hardeners and epoxide components may in addition contain extenders, such as coumarone oil, diluents, such as dibutyl phthalate, although they are preferably used without them, and reactive diluents, such as monoglycidyl esters or monoglycidyl ethers, e.g. reaction products of phenols with epichlorohydrin; catalysts for accelerating hardening, such as alcohols, phenols, tertiary amines or organic acids, such as salicylic acid or Lewis acids, such as BF$_3$, or adducts thereof with alcohols, phosphorus compounds, such as triphenyl phosphite, retarders to delay hardening, such as ketones or esters and also solid additives, fillers and reinforcing substances, such as talcum, quartz sand, titanium dioxide, kieselguhr, heavy spar, asbestos, glass fibres, zinc dust and mica, siccatives, thixotropic agents and pigments, such as iron oxide, chromium oxide and cadmium sulphide. UV stabilizers may also be added for external application. The resin compositions may vary advantageously also be used as aqueous emulsions.

The systems described are particularly advantageously used wherever cold setting epoxide resins are normally used, e.g. for the finishing of cast articles and resin mats, and especially in the field of paints and lacquers.

The substrates which may be covered or coated include metals, wood, paper, cardboard products, textiles, leather, glass, plastics, ceramics, stone, concrete.

The parts and percentages in the Examples refer to weight, unless otherwise indicated.

The outflow viscosities given in the Examples were determined according to DIN 53 211, using a 6 mm outflow cup.

Epoxide resin I used in the Examples is a bis-phenol-A-diglycidyl ether having an epoxide value of 0.55. Epoxide resin II is a mixture of epoxide resin I (70 parts) and 30 parts of t-butyl phenyl glycidyl ether, the p-t-butyl phenol used for production of the t-butyl phenyl glycidyl ether being a commercial mixture of o- and p-t-butyl phenol. The t-butyl phenol is reacted in known manner with epichlorohydrin in the presence of sodium hydroxide solution to produce the glycidyl ether. The epoxide value of epoxide resin II is 0.5.

The film properties given in the Examples were determined on films which had been obtained from the given epoxide/hardener mixture applied in layers of from 0.3 to 0.5 mm to glass plates and then dried at room temperature (ca. 23° C.) for 24 hours. The epoxide resin and hardener were used in equivalent proportions.

The films were assessed from the following aspects: freedom from tackiness, gloss, hardness, (scratch-resistance), surface faults (blooming effect, undulating faults, orange peel effect) and transparency.

The first pre-condition for the suitability of an epoxide resin at room temperature is, of course, the freedom from tackiness of the film (surface), which was determined as follows:

The support was placed with the lacquer layer upwards on a calibrated balance loaded with a counterweight of 1 kg. A small, fat-free wad of cotton wool from 2 to 3 cm in diameter was placed on the lacquer layer and on this wad was placed a small metal disc 2 cm in diameter. Finger pressure was then applied to the disc until the weighing machine was balanced and it was kept in balance for 10 seconds. After removal of the metal disc, attempts were made to remove the wad of cotton wool by gentle blowing. The lacquer layer is tack free when the wad no longer sticks to the lacquer layer and does not even leave small hairs on the surface.

EXAMPLE 1

(a) 184 g (about 0.5 mol) of n-pentadecane sulphonic acid phenyl ester containing about 7% of n-pentadecane disulphonic acid diphenyl ester and 278 g (about 1.2 mol) of pentaethylene hexamine are reacted for 2 hours at about 20 m bar and 180°–190° C., phenol being distilled off in the process.

A light brown oil having an outflow viscosity equivalent to 3.5 minutes and an NH equivalent of 48 is obtained.

A clear, smooth, scratch-resistant, virtually tack-free film is obtained from this hardener and epoxide resin I.

(b) 21 g (0.4 mol) of acrylonitrile are added in 30 minutes at 60° C. to 365 g of the oil prepared under (a). A light brown oil having an outflow viscosity equivalent to 4 minutes and an NH equivalent of 58 is obtained. Epoxide resins I and II prepared with this hardener give rise to glossy, smooth, very scratch-resistant and tack-free lacquer films.

(c) 100 g of product (a) are reacted with 7.5 g (0.05 mol) of phenyl glycidyl ether for 1 hour at from 50° to 60° C. When used with epoxide resin I, the oily hardener (outflow time 4.5 minutes), which has an NH equivalent of 72, provides clear, tackfree, scratch-resistant, elastic lacquer films.

EXAMPLE 2

Example 1(a) is repeated, but using 155 g (about 0.67 mol) instead of 278 g of pentaethylene hexamine. A brownish oil (outflow viscosity 4 min. NH equivalent is obtained which, when combined with epoxide resin I, gives rise to a smooth, clear, tack-free, scratch-resistant film, and, with epoxide resin II, it gives rise to an elastic, relatively soft, transparent resin plate which has a smooth, tack-free surface.

EXAMPLE 3

A mixture of,
75 g of triethylene tetramine (0.51 mol),
48 g of tetraethylene pentamine (0.25 mol),
40 g of pentaethylene hexamine (0.17 mol), and
368 g (1 mol) of the sulphonic acid ester of Example 1(a)

is heated to from 150° to 180° C. at 10 mbar, and phenol is distilled off through a 50 cm Vigreux column. The thick oil (outflow viscosity 7 min) which has an NH equivalent of 99 gives rise to elastic, transparent resin plates and films having a tack-free and smooth surface when used with epoxide resins I and II.

EXAMPLE 4

Example 3 is repeated, but using the following quantities of amine:
97 g ( about 0.66 mol) of triethylene tetramine,
62 g ( about 0.33 mol) of tetraethylene pentamine and
51 g ( 0.22 mol) of pentaethylene hexamine.

When the clear, light brown oil obtained, which had an outflow viscosity equivalent to 3 min 10 sec and an NH equivalent of 80, is combined with epoxide resins I and II, it gives rise to smooth, clear, tack-free and scratch-resistant lacquer films and elastic resin plates having a smooth, glossy surface.

EXAMPLE 5

(a) Example 1 is repeated, but using 232 g (1 mol) of pentaethylene hexamine. The resulting oil has an NH equivalent of 53 and an outflow time of 3.5 min and, when treated with epoxide resin II, it gives rise to scratch-resistant, smooth and tack-free lacquer films.

(b) 165 g of the product from 5(a) are reacted with 13 g of propylene oxide at 60° C. The NH equivalent is thereby increased to 61. The outflow time is 3.8 min. p Epoxides I and II give rise to scratch-resistant, tack-free, smooth lacquer films.

EXAMPLE 6

552 g (1.5 mol) of the sulphonic acid ester of Example 1(a) and 522 g (2.25 mol) of pentaethylene hexamine are condensed as in Example 1(a) and 135 g of phenol are distilled off. 932 g of a light brown, clear oil are obtained, which is subsequently reacted with 74 g (1.4 mol) of acrylonitrile at 60° C. for 30 minutes. The thick oil obtained has an NH equivalent of 88 and an outflow time of 4 minutes.

The lacquer films obtained with epoxide resin I are clear, elastic, tack-free, smooth and scratch-resistant. Those obtained with epoxide resin II are similar, but not yet completely scratch-resistant.

EXAMPLE 7

(a) A mixture of 900 g of the sulphonic acid ester used in Example 1(a) and 1278 g of pentaethylene hexamine are stirred at 150° C. under nitrogen for 5 hours and then reacted with 537 g of acrylonitrile for from 40 to 60 minutes at 60° C. When the yellow oil which has an NH equivalent of 98 is used with epoxide resin I, it gives rise to clear, scratch-resistant, tack-free, smooth lacquer films.

(b) The hardener according to 8(a) may also be used in aqueous systems. For this purpose, a solution of the hardener in 50% of its weight of water is prepared and vigorously mixed with epoxide resin I The emulsion obtained gives rise to clear, scratch-resistant, tack-free lacquer films. The addition of a very small quantity of solvent (from 1 to 2% based on the total quantity), such as xylene or n-butanol, accelerates the evaporation of water and even further improves the levelling flow so that the films obtained have a high gloss.

EXAMPLE 8

586 g (1 mol) of a mixture of n-tridecane- to n-octadecane-sulphonic acid phenyl esters, corresponding on average to n-pentadecane sulphonic acid phenyl esters and containing about 26% of mono-, 33% of di-, 24% of tri-, 12% of tetra- and from 4 to 5% of pentasulphonic acid ester, and 552 g (2.48 mol) of pentaethylene hexamine are stirred under nitrogen at from 150° to 160° C. for 7 hours.

The highly viscous, yellow brown resin obtained which has an NH equivalent of 106 is diluted with 50% of its weight of water and stirred with epoxide resin I to form an emulsion which, when spread coated, hardens to form clear, scratch-resistant, tack-free, glossy lacquer films.

The mixture of n-tridecane- to n-octadecanesulphonic acid phenyl esters consists of 6% of tridecane-, 27% tetradecane-, 33% of pentadecane 22% of hexadecane-, 10% of heptadecane- and 2% of octadecane-sulphonic acid phenyl esters.

EXAMPLE 9

586 g of the sulphonic acid ester used in Example 8 and 348 g (2.48 mol) of triethylene tetramine are stirred under nitrogen at from 150° to 160° C. for 7 hours and then reacted with 48 g (0.9 mol) of acrylonitrile at 60° C. The yellow brown resin (NH equivalent 117) is taken up in 50% of its weight of water and emulsified with epoxide resin I. The emulsion provides clear, scratch-resistant, tack-free and glossy lacquer films.

EXAMPLE 10

586 g of the sulphonic acid ester used in Example 8 and 450 g (2.48 mol) of tetraethylene pentamine are stirred under nitrogen at from 150° to 160° C. for 7 hours and then reacted with 104 g (1.95 mol) of acrylonitrile (NH equivalent 112) at 60° C. When the hardener is dissolved in 30% of its weight of water and stirred with epoxide resin I; the emulsion formed gives rise to clear, tack-free, glossy and scratch-resistant lacquer coats.

EXAMPLE 11

(a) 150 g (0.65 mol of the sulphonic acid ester of Example 9 and 60 g (0.36 mol) of pentaethylene hexamine are heated to 160° C. for 1 hour. The yellow brown, thick resin obtained is watersoluble. NH-equivalent=272.

This hardener is stirred with about 20% of its weight of water to form an oil. After the additon of the equivalent quantity of epoxide resin I, a stable, finely divided emulsion is obtained simply by stirring without the aid of emulsifier or high speed stirrer. When spread coated, this emulsion forms clear, tack-free and glossy lacquer films.

(b) 102 g of the resin obtained as described under (a) are heated to a sump temperature of 190° C. at 19 mbar and freed from phenol. NH equivalent=216. The highly viscous resin is mixed with 4 times its quantity of water to form a thin, clear oil. The equivalent quantity of epoxide resin I may be converted into a stable, finely divided emulsion having a pot life of from 2 to 2½ hours simply by stirring it as under (a). This emulsion give rise to clear, glossy lacquer films which have hardened sufficiently to be tack-free after only from 6 to 7 hours.

EXAMPLE 12

A mixture of 312 g (1 mol), based on the sulphonate group, of n-pentadecane-sulphonic acid phenyl ester containing about 25% of disulphonate and 232 g (1 mol) of pentaethylene hexamine is freed from phenol after 5 hours' stirring at 160° C. under nitrogen at 10 mbar at a sump temperature upto 190° C. A light brown, thick oil having an Outflow viscosity equivalent to 25 minutes and an NH equivalent of 78 is obtained. The product forms a clear solution in cold water. A smooth, clear and scratch-resistant lacquer film is obtained with epoxide resin I.

EXAMPLE 13

A mixture of 312 g (1 mol) of n-pentadecanesulphonic acid phenyl ester containing 25% of disulphonic acid phenyl ester and 182 g (1 mol) of tetraethylene pentamine is stirred for 5 hours at 160° C. under nitrogen and then freed from phenol at a sump temperature of 190° C. A brownish oil having an outflow viscosity equivalent to 22 minutes and an NH equivalent of 86 is obtained. The product forms a clear solution in cold water. A clear, glossy, scratch-resistant lacquer film is obtained with epoxide resin I.

EXAMPLE 14

A mixture of 312 g (1 mol) of n-pentadecanesulphonic acid phenyl ester containing about 25% of disulphonic acid phenyl ester and 146 g (1 mol) of triethylene tetramine is stirred for 7 hours under nitrogen at 160° C. and then freed from phenol at 10 mbar up to a sump temperature of 190° C. A thick, yellow brown oil having an outflow viscosity equivalent to 18 minutes and an NH equivalent of 93 is obtained. The product forms a clear solution in cold water. A clear, glossy and scratch-resistant lacquer film is obtained with epoxide resin I.

EXAMPLE 15

The hardeners from Examples 12 to 14 are tested and compared for activity by rapidly mixing hardener and epoxide resin in quantities corresponding to the NH equivalents thereof and reacting 100 g of this mixture under controlled temperature conditions in a cylindrical insulating vessel. The more rapidly the temperature of the mixture rises, i.e. the shorter the time required to reach a certain temperature, the higher is the activity of the hardener. For the sake of comparison, the time measured is that required for the temperature to rise from 22° C. to 50° C.

The following Table gives the composition and data of the hardeners from Examples 12 to 14 and the reaction times measured.

| Ex. No. | Mol SPE* | Mol PPA* | Number of basic NH in molecule of hardener | NH equivalent | Parts of epoxide I | Parts of hardener | Reaction time from 22° C.–50° C. |
|---|---|---|---|---|---|---|---|
| 12 | 1 | 1 Pentaethylene hexamine | 6 | 78 | 70 | 30 | 30 min. |
| 13 | 1 | 1 Tetraethylene pentamine | 5 | 86 | 68 | 32 | 21 min. |
| 14 | 1 | 1 Triethylene tetramine | 4 | 93 | 66 | 34 | 14 min. |

*SPE = sulphonic acid phenyl ester
*PPA = polyethylene polyamine

From the Table it may be seen that the higher the NH equivalent or the smaller the number of basic NH groups in the molecule of hardener, the shorter is the reaction time and hence the greater the activity. This is a completely unexpected finding.

Commercial carboxylic acids structurally as similar as possible to the alkane sulphonic acid derivatives are used for the comparison experiments. These carboxylic acids are condensed to carbonamide amines with the same polyamines as those used for the production of the sulphonamidamines.

COMPARISON EXPERIMENT 1

(Comparison to Example 1)

A mixture of 236 g (1 mol, based on the COOH group) of palmitic acid ($C_{16}$ carboxylic acid) containing 7 mol % of dodecane diacid (analogous to the sulphonate mixture in Example 1) and 310 g (1.34 mol) of pentaethylene hexamine is heated to 160° C. with stirring under nitrogen, and the mixture begins to condense with elimination of water. After from 5 to 6 hours, a sump temperature of 200° C. has been reached and most of the water has been removed. Dehydration is then continued for a further 4 hours ar 10 mbar. At the end of this time, the calculated quantity of water has been distilled off. A viscous oil is obtained which is yellowish in the heat. On cooling, it slowly solidifies to a solid, hard cake. NH equivalent=49. The carbonamidamine is water-soluble only in the heat and insoluble in xylene and ethanol at room temperature.

To use the product for hardening, it is melted, chilled so that it remains liquid for a short time, rapidly mixed with epoxide resin I and applied by spread coating. The film obtained is completely opaque and readily flakes off.

COMPARISON EXPERIMENT 2

(Comparison to Example 1)

A mixture of 257 g (1 mol, based on COOH group) of palmitic acid containing 7 mol % of dimeric fatty acid (prepared from unsaturated $C_{18}$ acids) and 310 g (1.34 mol) of pentaethylene hexamine is condensed as in comparison experiment 1. An oil which is yellowish in the heat and slowly solidifies on cooling to a solid, waxy product is obtained. NH equivalent=52. The carbonamidamine is water-soluble only in the heat. In xylene and ethanol, the product is insoluble at room temperature.

When the product is used for hardening, it is melted, chilled so that it remains a thick liquid for a short time, rapidly mixed with epoxide resin I and applied by spread coating. The film obtained is cloudy and easily flakes off. When the mixture is diluted with water, an unstable emulsion is obtained which, when spread coated, forms a cloudy, tacky film.

COMPARISON EXAMPLE 3

(Comparison with Example 2)

A mixture of 173 g (0.68 mol) of palmitic acid, 53 g (0.225 mol) dodecane diacid and 232 g (1 mol) od pentaethylene hexamine is condensed with elimination of water by reacting it under nitrogen and stirring as in comparison Example 1. The product obtained is a viscous, yellow oil in the heat and solidifies to a solid block on cooling. NH equivalent=77.

The carbonamidamine is water-soluble only in the heat and is incompatible with epoxide resins I and II.

COMPARISON EXAMPLE 4

(Comparison with Example 12)

A mixture of 197 g (0.77 mol) of palmitic acid, 66 g ( 0.118 mol) of dimeric fatty acid (from unsaturated $C_{18}$ acids) and 232 g (1 mol) of pentaethylene hexamine is condensed with elimination of water as in comparison Example 1. A product which is a viscous, yellow oil in the heat and solidifies to a solid block on cooling is obtained. NH equivalent=79.

The carbonamidamine is difficult to dissolve in water even when heated and is completely incompatible with epoxide resins I and II.

COMPARISON EXAMPLE 5

(Comparison with Example 14)

A mixture of 170 g (0.665 mol) of palmitic acid, 52 g (0.221 mol) of dodecane diacid and 146 g (1 mol) of triethylene tetramine is condensed as in comparison Example 1. The product obtained is a viscous, yellow oil in the heat and solidifies to a solid block on cooling. NH equivalent=92.

The carbonamidamine is insoluble in water even in the heat.

COMPARISON EXAMPLE 6

(Comparison with Example 14)

A mixture of 185 g (0.72 mol) of palmitic acid, 62 g (0.11 mol) of dimeric fatty acid and 146 g (1 mol) of triethylene tetramine is reacted as in Comparison Example 1. A hot, viscous, yellow oil is obtained, which solidifies to a solid block on cooling. NH equivalent=91.

The carbonamidamine is insoluble in water even in the heat.

We claim:
1. A sulphonic acid amidamine corresponding to the formula (I):

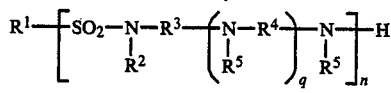

wherein the SO₂ group is obtained from a SO₂Cl group introduced into the molecule by sulfochlorination and wherein:

$R^1$ represents a $C_{10}$-$C_{18}$ linear, saturated aliphatic hydrocarbon group which is unsubstituted or substituted by one or more chlorine atoms;

$R^2$ and $R^5$ independently each represent hydrogen, $C_1$-$C_6$ alkyl, $C_1$-$C_6$ alkyl substituted with hydroxyl, amino, mercapto, cyano, carboxyl or carbamoyl, or said alkyl interrupted by at least one —O— or —S— group;

$R^3$ and $R^4$ independently represent $C_2$-$C_{13}$ alkylene, $C_5$-$C_7$ cycloalkylene, or said alkylene or cycloalkylene group hydroxyl, amino, mercapto, cyano, carboxyl or carbamoyl; q represents zero or an interger of from 1 to 12; and n represents an integer of from 1 to 8.

2. A process for the production of a sulphonic acid amidamine as claimed in claim 1 which comprises reacting 1 equivalent of a sulphonic acid derivative corresponding to the following general formula (II):

$$R^1 (SO_2X)_n \quad (II)$$

wherein $R^1$ and n are as defined in claim 1; and X represents —O—aryl; with from 0.3 to 3.0 mol of amine corresponding to the following general formula (III):

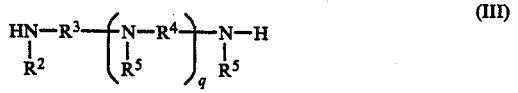

wherein $R^2$, $R^3$, $R^4$, $R^5$ and q are as defined in claim 1; at a temperature of from 80° to 280° C. with elimination of HX.

3. A composition comprising a sulphonic acid amidamine corresponding to the formula

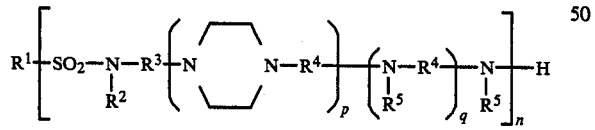

wherein the SO₂ group is obtained from an SO₂Cl group introduced into the molecule by sulfochlorination and wherein:

$R^1$ represents a $C_{10}$-$C_{18}$ linear, saturated aliphatic hydrocarbon group which is unsubstituted or substitutdd by one or more chlorine atoms;

$R^1$ and $R^5$ independently each represent hydrogen, $C_1$-$C_6$ alkyl, $C_1$-$C_6$ alkyl substituted with hydroxyl, amino, mercapto, cyano, carboxyl or carbamoyl, or said alkyl interrupted by at least on —O— or —S— group;

$R^3$ and $R^4$ independently represent $C_2$—$C_{13}$ alkylene, $C_5$-$C_7$ cycloalkylene group substituted with hydroxyl, amino, mercapto, cyano, carboxyl or carbamoyl;

p represents zero or an integer of from 1 to 12; and
n represents an integer of from 1 to 8 and;
an epoxide having at least one 1,2-epoxide group.

4. A process for preparing a supphonic acid amidamine corresponding to the formula:

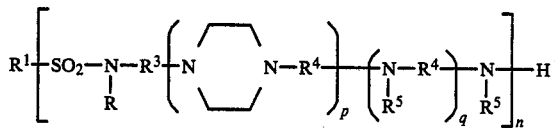

wherein:
$R^1$ represents a $C_1$-$C_{18}$ linear, saturated aliphatic hydrocarbon group which is unsubstituted or substituted by one or more chlorine atoms;

$R^2$ and $R^5$ independently each represent hydrogen, $C_1$-$C_6$ alkyl, $C_1$-$C_6$ alkyl substituted with hydroxyl, amino, mercapto, cyano, carboxyl or carbamoyl, or said alkyl interrupted by at least one —O— or —S— group;

$R^3$ and $R^4$ independently repersent $C_1$-$C_{13}$ alkylene, $C_5$-$C_7$ cycloalkylene, or said alkylene or cycloalkylene group substituted with hydroxyl, amiono, mercapto, cyano, carboxyl or carbamoyl;

p represents zero or 1;
q represents zero or an integer of from 1 to 12; and
n which represents an integer of from 1 to 8;
which comprises reacting 1 equivalent of a sulphonic acid derivative corresponding to the formula $$R^1 (SO_2X)_n$$

wherein X represents —O— aryl; with from 0.3 to 3.0 mol of amino corresponding to the formula

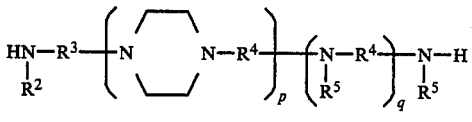

at a temperature of from 80° to 280? C., with elimination of HX.

* * * * *